United States Patent [19]

Smirmaul

[11] Patent Number: 4,959,049
[45] Date of Patent: Sep. 25, 1990

[54] TIP FOR A PHACOEMULSIFICATION NEEDLE

[76] Inventor: Heinz J. Smirmaul, 1307 Brookstone La., Duncanville, Tex. 75137

[21] Appl. No.: 405,525

[22] Filed: Sep. 11, 1989

[51] Int. Cl.⁵ .............................................. A61B 17/20
[52] U.S. Cl. ....................................... 604/22; 606/161
[58] Field of Search .................. 604/22, 46, 164, 170, 604/239, 294, 264, 272–274; 606/160–161, 223, 159, 167, 187, 189

[56] References Cited

U.S. PATENT DOCUMENTS

| | | | |
|---|---|---|---|
| 3,110,304 | 11/1963 | Hartman | 606/160 X |
| 3,955,579 | 5/1976 | Bridgman | 604/22 X |
| 3,996,935 | 12/1976 | Banko | 604/22 |
| 4,681,102 | 7/1987 | Bartell | 128/303 R |
| 4,689,040 | 8/1987 | Thompson | 604/22 |
| 4,808,154 | 2/1989 | Freeman | 604/21 |
| 4,838,853 | 6/1989 | Parisi | 604/22 |
| 4,850,354 | 7/1989 | McGurk-Burleson et al. | 604/22 X |

*Primary Examiner*—C. Fred Rosenbaum
*Assistant Examiner*—c. Maglione
*Attorney, Agent, or Firm*—Ross, Howison, Clapp & Korn

[57] ABSTRACT

An improved tip for a phacoemulsification needle having a proximal end attached to a phacoemulsification device, a distal end, a central longitudinal axis extending from the proximal end to the distal end with a bore within the needle concentric to the central axis thereof, so as to form a lumen, the lumen includes needle sidewalls having an inner and outer surface with an opening at the proximal and distal ends of the needle, the tip is formed by the distal opening which, when viewed from an angle perpendicular to the central longitudinal axis has a side view including a top wall located at a needle sidewall on one side of the central longitudinal axis. The top wall terminates in a top wall end face. The needle tip further includes a bottom wall located at a needle sidewall on the opposite side of the central longitudinal axis and extending distal of the end face of said top wall to form a tip projection. An end wall is disposed generally perpendicular to the tip projection. An arcuate portion interconnects the tip projection and the end wall. A tip projection sidewall extends from the needle sidewall and the tip projection to the height of the end wall and terminates in a tip projection sidewall face being generally parallel to the tip projection.

3 Claims, 1 Drawing Sheet

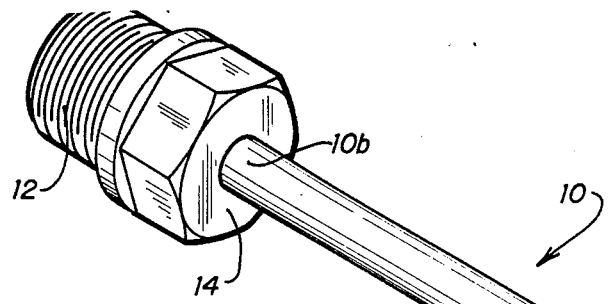
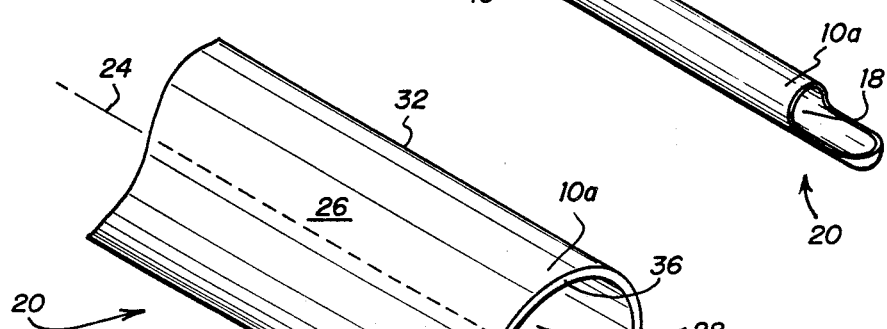
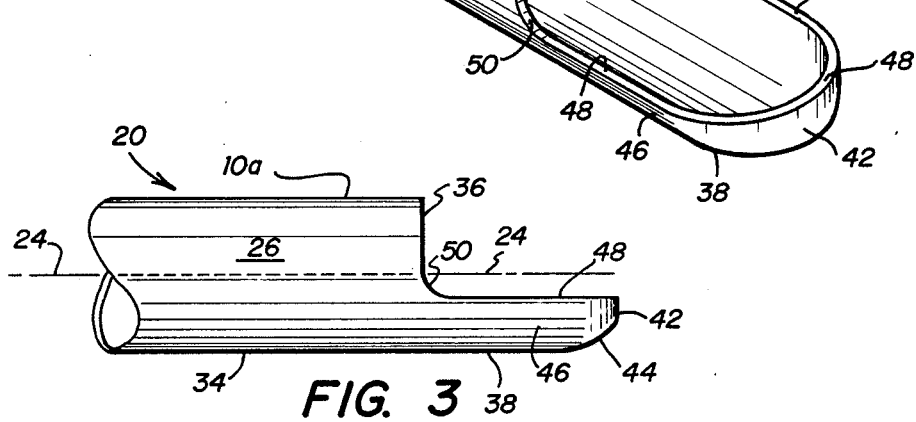
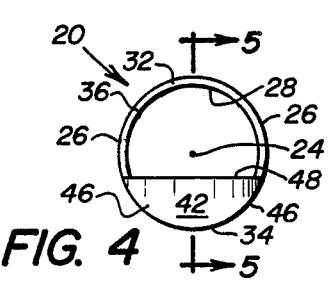
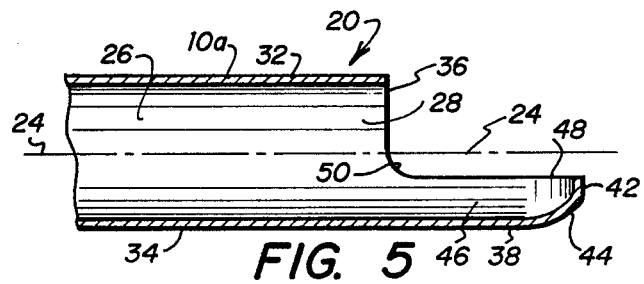

TIP FOR A PHACOEMULSIFICATION NEEDLE

TECHNICAL FIELD OF THE INVENTION

This invention relates to surgical instruments, and more particularly to an improved tip for a phacoemulsification needle.

BACKGROUND OF THE INVENTION

A phacoemulsification surgical instrument provides for the breaking apart and the removal of unwanted tissue and material, especially a cataract located in the anterior chamber of the eye, by ultrasonically fragmenting the cataract while simultaneously introducing fluid into the eye chamber and withdrawing the fluid and fragmented cataract particles. A phacoemulsification instrument includes a handpiece having an operative needle vibrating in the ultrasonic range. The needle shaft is hollow and is in turn surrounded by a tubular sleeve. In operation, the needle shaft including the surrounding tubular sleeve is inserted into the anterior chamber of the eye. Irrigation fluid is introduced through the hollow sleeve to provide a replacement for fluid withdrawn or lost from the eye chamber during surgery. The needle tip is used to emulsify the cataract.

It is desirable to emulsify the lens nucleus in situ because removing the nucleus from its original position and emulsifying the nucleus elsewhere in the eye creates a possibility of damage to other eye tissue, such as damage to the iris and corneal endothelium. However, emulsification of the lens in situ causes additional problems, particularly the danger of rupturing the posterior capsule. If the posterior capsule encounters a sharp instrument, particularly a vibrating needle, the posterior capsule may be easily punctured, and once its structural integrity is broken, the posterior capsule generally splits and tears. Damage to the posterior capsule results in the loss of vitreous humor and lens particles and other material falling into the posterior chamber resulting in undesirable complications, dangers and difficulties in performing cataract surgery and patient recovery.

A need has thus arisen for a phacoemulsification needle having a tip which greatly reduces the probability of posterior capsule rupture, especially when the lens is emulsified in its original position.

SUMMARY OF THE INVENTION

In accordance with the present invention, an improved tip for a phacoemulsification needle having a proximal end attached to a phacoemulsification device and a distal end inserted into the eye is provided. The needle includes a central longitudinal axis extending from the proximal end to the distal end with a bore within the needle concentric to the central longitudinal axis thereof, so as to form a lumen. The lumen includes needle sidewalls having an inner and outer surface with an opening at the proximal and distal ends of the needle. The tip is formed by the distal end opening which, when viewed from an angle perpendicular to the central longitudinal axis has a side view including a top wall located at a needle sidewall on one side of the central longitudinal axis. The top wall terminates in a top wall end face. The needle tip further includes a bottom wall located at a needle sidewall on the opposite side of the central longitudinal axis and extending distal of the end face of said top wall to form a tip projection. An end wall is disposed generally perpendicular to the tip projection. An arcuate portion interconnects the tip projection and the end wall. A tip projection sidewall extends from the needle sidewall and the tip projection to the height of the end wall and terminates in a tip projection sidewall face being generally parallel to the tip projection.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which:

FIG. 1 is perspective view of a typical phacoemulsification needle having the improved tip of the present invention;

FIG. 2 is a perspective view of the present phacoemulsification needle tip;

FIG. 3 is a side view of the present phacoemulsification needle tip shown in FIG. 2;

FIG. 4 is an end view of the present phacoemulsification needle tip shown in FIG. 2; and FIG. 5 is a cross-sectional view, taken generally along sectional lines 5—5 of FIG. 4, illustrating the present phacoemulsification needle tip.

DESCRIPTION OF THE PREFERRED EMBODIMENTS

Referring to FIG. 1, a typical phacoemulsification needle, generally referred to by the numeral 10 is illustrated. Phacoemulsification needle 10 includes a distal end 10a and a proximate end 10b. Phacoemulsification needle 10 can be utilized in any ultrasonic system for the break-up and removal of tissue, and is not limited to the break-up and removal of eye lens material, it being understood that such systems, including the present invention, are applicable to many other uses. Phacoemulsification needle 10 includes a threaded rear portion 12 and a nut 14 at proximate end 10b for attaching phacoemulsification needle 10 to a handpiece (not shown) of the phacoemulsification system for vibrating phacoemulsification needle 10 in the ultrasonic range. Phacoemulsification needle 10 includes an elongated, thin-walled shaft 16 having a lumen 18 and a tip generally identified by the numeral 20. Phacoemulsification needle 10 may have an outside diameter of 0.030-0.050 inches and a wall thickness of approximately 0.0035 inches. In cross-section, shaft 16 may be circular as illustrated in FIGS. 1-5, or slightly elliptical.

Referring simultaneously to FIGS. 2-5, phacoemulsification tip 20 is formed as an extension from distal end 10a of phacoemulsification needle 10 and is insertable into the eye during surgical procedures. Phacoemulsification needle 10 includes a central longitudinal axis 24 extending from proximal end 10b to distal end 10a of phacoemulsification needle 10. Lumen 18 is concentric to central longitudinal axis 24 and is defined by a circular sidewall 26 which extends around central longitudinal axis 24. Tip 20 is formed around a distal opening 28 formed in distal end 10a of phacoemulsification needle 10.

Sidewall 26 of phacoemulsification needle 10 includes a top wall 32 located on one side of central longitudinal axis 24, and a bottom wall 34 located on the other side of central longitudinal axis 24 along sidewall 26. Top wall 32 terminates in a top wall end face 36. Bottom wall 34 of sidewall 26 extends past top wall 32 and distal opening 28 of phacoemulsification needle 10 to form a tip projection 38. Tip projection 38 is an extension of bottom wall 34 of phacoemulsification needle 10.

Tip 20 further includes an end wall 42 disposed generally perpendicular to tip projection 38. End wall 42 extends approximately one-third the separation between top wall 3 and bottom wall 34. An arcuate portion 44 interconnects tip projection 38 and end wall 42. A tip projection sidewall 46 extends from sidewall 26 of phacoemulsification needle 10 and from tip projection 38 to the height of end wall 42, and forms a tip projection sidewall face 48, generally parallel to tip projection 38. An arcuate portion 50 interconnects sidewall 26 and tip projection sidewall face 48.

Top wall end face 36, arcuate portion 50, and tip projection sidewall face 48 include a cutting surface for break-up and sculpturing of lens material to be severed during a surgical operation. Arcuate portion 44 of tip projection 38 is smooth and therefore prevents posterior capsule rupture during use of phacoemulsification needle 10. Tip 20 forms a general scoop-like needle tip for phacoemulsification needle 10 and may be used for sculpturing material, for severing material from other material, and for holding and moving material to positions where such material may be safer to aspirate and emulsify.

Whereas the present invention has been described with respect to specific embodiments thereof, it will be understood that various changes and modifications will be suggested to one skilled in the art and it is intended to encompass such changes and modifications as fall within the scope of the appended claims.

What is claimed:

1. In a phacoemulsification needle with a proximal end attachable to a phacoemulsification device and a distal end insertable into material to be emulsified; the needle having a central longitudinal axis extending from the proximal end to the distal end; the phacoemulsification device oscillating the needle in the direction of the central longitudinal axis; a bore within the needle concentric to the central longitudinal axis thereof, thereby forming a lumen, the lumen having needle sidewalls therearound, having inner and outer surfaces with an opening at the proximal and distal ends of the needle, an improved tip comprising:

a tip formed by the distal opening which when viewed from an angle perpendicular to the central longitudinal axis has a side view comprising:

a top wall located at a needle sidewall on one side of the central longitudinal axis and terminating in a top wall end face disposed in a plane generally perpendicular to the central longitudinal axis, said top wall end face including a cutting surface for cutting the material to be emulsified in the direction of needle oscillation;

a bottom wall located at a needle sidewall on the opposite side of the central longitudinal axis and extending distal of said top wall end face to form a tip projection;

an end wall disposed generally perpendicular to said tip projection and disposed in a plane generally parallel to the plane of said top wall end face;

an arcuate portion interconnecting said tip projection and said end wall; and a tip projection sidewall extending from the needle sidewall to said end wall and from said tip projection to the height of said end wall and terminating in a tip projection sidewall face, said tip projection sidewall face being generally parallel to said top projection and generally perpendicular to said top wall end face and further including a cutting surface for cutting the material to be emulsified in a direction generally perpendicular to the cuts made by said top wall end face as the needle is moved generally perpendicular to the direction of needle oscillation through the material to be emulsified.

2. The phacoemulsification tip of claim 1 and further including:

an arcuate portion including a cutting surface interconnecting the needle sidewall and said tip projection sidewall face.

3. The phacoemulsification tip of claim 1 wherein said end wall extends from said bottom wall for approximately one-third of the separation between said top and bottom walls.

* * * * *